(12) United States Patent
Acey et al.

(10) Patent No.: US 6,750,056 B2
(45) Date of Patent: Jun. 15, 2004

(54) METAL BINDING PROTEINS AND ASSOCIATED METHODS

(76) Inventors: Roger A. Acey, 17634 Virginia, Bellflower, CA (US) 90706; Michael Mustillo, 210 Euclid, Apt. B., Long Beach, CA (US) 90803; Brenton G. Harpham, 3270 Big Sky Dr., Thousand Oaks, CA (US) 91360

( * ) Notice: Subject to any disclaimer, the term of this patent is extended or adjusted under 35 U.S.C. 154(b) by 0 days.

(21) Appl. No.: 09/948,495

(22) Filed: Sep. 6, 2001

(65) Prior Publication Data

US 2003/0105304 A1 Jun. 5, 2003

(51) Int. Cl.[7] .................. C12N 15/12; C12N 15/67; C12N 1/13; C12N 1/21; C12N 5/10
(52) U.S. Cl. .................. 435/325; 435/320.1; 435/410; 435/252.3; 435/254.11; 536/23.2; 536/23.5
(58) Field of Search .................. 435/325, 410, 435/252.3, 254.11, 320.1, 455, 468, 471; 536/23.2, 23.5, 23.1

(56) References Cited

U.S. PATENT DOCUMENTS

| | | | |
|---|---|---|---|
| 5,814,480 A | 9/1998 | Hillman et al. | 435/69.1 |
| 5,824,512 A | 10/1998 | Pazirandeh et al. | 435/69.7 |

OTHER PUBLICATIONS

Mokdad et al., GenBank Acc. No. M16250, US National Library of Medicine, Bethesda, MD, Apr. 26, 1993, accessed by PTO on Jul. 29, 2003.*

Ngo et al., "Computational complexity, protein structure prediction, and the Levinthal paradox", in The Protein Folding Problem and Tertiary Structure Prediction, Merz et al. (eds.), Birkhauser Boston: Boston, MA, pp. 433 and 492–495.*

Rudinger, "Characteristics of the amino acid as componants of a peptide hormone sequence", in Peptide Hormones, Parsons (ed.), University Park Press: Baltimore, MD, pp. 1–7.*

Kennell, D.E., "Principals and practices of nucleic acid hybridization", Progr. Nucleic Acid Res. Mol. Biol. 11: 259–301.*

Article entitled Commentary: "Recent excitement regarding metallothionein", Proc. Natl. Acad. Sci. USA, vol. 95, pp. 333–334, by Edmond H. Fischer and Earl W. Davie, dated Mar., 1998.

Metallothionein[1,2], Ann. Rev. Biochem., 1986, 55:913–51, by Dean H. Hammer.

"Notice", regarding publication developed under Grant No. CX824823 awarded by the U.S. EPA.

"Primary structures of decapod crustacean metallothioneins with special emphasis on freshwater and semi–terrestrial species", Biochem J. (1996) 319, 999–1003, by Pedersen, Pedersen, Hojrup, Depledges, and Knudsen.

Article from web site entitled "Recent Developments for In Situ Treatment of Metal Contaminated Soils", prepared for U.S. EPA, by Carl Ma & John Kinscott, and Mark Evans of PRC Enviromental Management, Inc., dated Mar. 5, 1997. Web site at http://www.clu–in.org//download/remed/metals2.pdf.

Article from Technology Evaluation Report entitled "Remediation of Metals–Contaminated Soils and Groundwater" prepared for GWRTAC by C. R. Evanko, Ph.D. and D.A. Dzombak, Ph.D., P.E., dated Oct. 1997.

\* cited by examiner

*Primary Examiner*—Scott D. Priebe
(74) *Attorney, Agent, or Firm*—Louis C. Cullman

(57) ABSTRACT

Metal binding proteins, associated compositions and methods for their production and use are disclosed. The metal binding proteins include have amino acid sequences analogous to at least one metal binding protein, and conservative amino acid substitutions thereof from a brine shrimp (Artemia). Also provided are the associated nucleic acid sequences encoding metal binding proteins.

16 Claims, 1 Drawing Sheet

SEQUENCE LISTING

<160> NUMBER OF SEQ ID NOS: 10

<210> SEQ ID NO 1
<211> LENGTH: 147
<212> TYPE: DNA
<213> ORGANISM: Artemia

<400> SEQUENCE: 1

```
atggactgct gcaagaacgg ttgcacctgt gccccaaatt gcaaatgtgc caaagactgc      60
aaatgctgca aaggttgtga gtgcaaaagc aacccagaat gcaaatgtga gaagaactgt     120
tcatgcaact catgtggttg tcactga                                         147
```

<210> SEQ ID NO 2
<211> LENGTH: 48
<212> TYPE: PRT
<213> ORGANISM: Artemia

<400> SEQUENCE: 2

Met Asp Cys Cys Lys Asp Gly Cys Thr Cys Ala Pro Asp Cys Lys Cys
1               5                   10                  15

Ala Lys Asp Cys Lys Cys Cys Lys Gly Cys Glu Cys Lys Ser Asp Pro
            20                  25                  30

Glu Cys Lys Cys Glu Lys Asp Cys Ser Cys Asp Ser Cys Gly Cys His
    35              40                  45

<210> SEQ ID NO 3
<211> LENGTH: 66
<212> TYPE: DNA
<213> ORGANISM: Artemia

<400> SEQUENCE: 3
atggactgct gcaagaacgg ttgcacctgt gccccaaatt gcaaatgtgc caaagactgc    60
aaatgc                                                              66

<210> SEQ ID NO 4
<211> LENGTH: 22
<212> TYPE: PRT
<213> ORGANISM: Artemia

<400> SEQUENCE: 4

Met Asp Cys Cys Lys Asp Gly Cys Thr Cys Ala Pro Asp Cys Lys Cys
 1               5                  10                  15

Ala Lys Asp Cys Lys Cys
            20

<210> SEQ ID NO 5
<211> LENGTH: 34
<212> TYPE: DNA
<213> ORGANISM: Artificial Sequence
<220> FEATURE: 5' primer (N-terminal side) utilized in PCR
      Amplification of Artemia Metal Binding Protein
      Sequences
<223> OTHER INFORMATION: :

<400> SEQUENCE: 5
acctatgcgg ccgcaaatgg actgctgcaa gaac                               34

<210> SEQ ID NO 6
<211> LENGTH: 31
<212> TYPE: DNA
<213> ORGANISM: Artificial Sequence
<220> FEATURE: 3' primer (C-terminal side) utilized in PCR
      Amplification of Artemia Metal Binding Protein
      Sequences
<223> OTHER INFORMATION: :

<400> SEQUENCE: 6
gcaccaacta gtgccttttt tttttttttt a                                  31

<210> SEQ ID NO 7
<211> LENGTH: 31
<212> TYPE: DNA
<213> ORGANISM: Artificial Sequence
<220> FEATURE: 3' primer (C-terminal side) utilized in PCR
      Amplification of Artemia Metal Binding Protein
      Sequences
<223> OTHER INFORMATION: :

<400> SEQUENCE: 7
gcaccaacta gtgccttttt tttttttttt c                                  31

<210> SEQ ID NO 8
<211> LENGTH: 31
<212> TYPE: DNA
<213> ORGANISM: Artificial Sequence
<220> FEATURE: 3' primer (C-terminal side) utilized in PCR
      Amplification of Artemia Metal Binding Protein -continued

```
       Sequences
<223> OTHER INFORMATION: :

<400> SEQUENCE: 8
gcaccaacta gtgccttttt tttttttttt g                              31

<210> SEQ ID NO 9
<211> LENGTH: 33
<212> TYPE: DNA
<213> ORGANISM: Artificial Sequence
<220> FEATURE: Primers which contain modifying restriction sites
      incorporated into their sequence; used to subclone
      the purified PCR product containing brine shrimp
      Artemia metal binding protein gene sequences.
      (5' primer containing an Nde I site)
<223> OTHER INFORMATION: :

<400> SEQUENCE: 9
gctacacata tgtccatgga ctgctgcaag aac                            33

<210> SEQ ID NO 10
<211> LENGTH: 31
<212> TYPE: DNA
<213> ORGANISM: Artificial Sequence
<220> FEATURE: Primers which contain modifying restriction sites
      incorporated into their sequence; used to subclone
      the purified PCR product containing brine shrimp
      Artemia metal binding protein gene sequences.
      (3' primer containing an Sal I site)
<223> OTHER INFORMATION: :

<400> SEQUENCE: 10
acgaacgtcg acgccttttt tttttttttt a                              31
```

METAL BINDING PROTEINS AND ASSOCIATED METHODS

BACKGROUND OF THE INVENTION

1. Field of the Invention

The present invention relates generally to unique metal binding proteins having high binding affinity for heavy metals. More particularly, the present invention is directed to compositions including the unique metal binding proteins and to associated methods of production and use where reduction or recovery of heavy metals is desired.

2. General Background and State of the Art

Metal recovery and metal remediation and the associated need for efficient and safe methods for clean up of metal waste is a continuing environmental and business concern due to the toxicity and potential risk to human health posed by metal contaminants, as well as the economic value of precious heavy metals. Indeed, as the discharge of toxic wastes such as heavy metals from agricultural, industrial and other commercial operations continues, the need for effective, safe and low-cost metal remediation methods increases. In a recent report by the U.S. EPA, metal contamination remains and historically has been a key concern at many contaminated sites (USEPA Work Assignment #011059, Mar. 5, 1997, Contract #68-W5-0055). In addition, there are numerous published reports of damage to wildlife, livestock, plantlife as well as danger to human health as a result of metal poisoning from contaminated soil or waste matter (Impact of Lead-Contaminated Soil on Public Health by Xintaras, C. May 1992 at http://www.atsdr.cdc.gov/cxlead.html). For example, a primary concern to humans is the health hazard created by lead (Pb) contamination. Exposure to lead can occur through a variety of methods such as by ingestion of lead from food, water, soil, or even inhalation of dust. Lead poisoning is extremely dangerous and potentially fatal, with symptoms including seizures, mental retardation and behavioral disorders. Therefore, methods for metal remediation are extremely valuable both for their protection of our environment as well as for protection from diseases.

Recovered metals from various waste, discard or recycling efforts provide immense economic value as well as augmenting environmental pollution control. Metal recovery can be from innumerable and varied sources such as from waste electronic devices (transistors, chips, transformers, bus bars, cathodes, and microprocessors, populated computer circuit boards PCBs, motherboards). Costs associated with hazardous disposal of industrial waste in the absence of metal reclamation are enormous. Therefore, metal recycling or reuse of metal extracted from scrap or discarded metal-containing items not only reduces the volume and cost of metal waste requiring specialized disposal and handling efforts, but the reclaimed metal can also be resold or reused to provide additional economic value.

Prior art attempts at treating metal contamination have traditionally employed cleanup technologies which consist primarily of physically removing and then disposing of contaminated matter. These methodologies are not only labor intensive and less efficient, but also carry a high expense associated with removal and disposal of large or bulk quantities of contaminated waste. Metal contamination is especially difficult to remediate because unlike other types of waste such as chemical or organic matter, metals cannot be directly destroyed or converted. For example, current technologies for remediating metal contaminated soils consist primarily of landfilling or soil excavation with physical or chemical separation of the metal contaminants. Treatment of contaminated ground water usually involves flushing, filtration or chemical extraction to remove the contaminating metals. As a result, the cost of soil or ground water remediation is high, ranging in the hundreds to thousands of millions of dollars in projected five-year costs per site (U.S. EPA, 1993).

In addition, the risk to humans and the environment from heavy metal contamination is not limited to soil or ground water, but also includes other sources such as industrial waste, sludge waste, wastewater, radionuclides (such as from research and medical waste) and mining waste. Depending on the physical and chemical form of the metal contaminant to be removed, as well as the cost-benefit analysis for a particular remediation approach, which of the existing technologies is better suited for a particular site will vary. However, due to the high cost of traditional cleanup technologies, there still remains a great need for a less-expensive, safe and effective heavy metal recovery and cleanup technology.

There are some technologies currently available for the recovery or remediation of heavy metal contaminated waste. In general, these technologies combine one or more of the following general approaches: isolation, immobilization, toxicity reduction, physical separation or extraction of metal contamination from a waste product. Isolation technologies utilize a containment strategy in an attempt to confine a contaminated site or area so as to prevent further spread of the toxic metal waste. Immobilization technologies reduce the mobility of metal contaminants and include systems which provide an impermeable barrier to separate underlying layers of soil (containing the metal contaminants) from the topsoil layer. Also used are physical barriers which restrict the flow of uncontaminated groundwater through a contaminated site. Additionally, there are toxicity reduction processes which generally use chemical or biological techniques to decrease the toxicity or mobility of metal contaminants. Included in toxicity reduction processes are biological treatment technologies, which apply newer biotechnical approaches.

Metal remediation is a relatively new application of biological treatment technologies and includes processes such as bioaccumulation, phytoremediation, phytoextraction, and rhizofiltration. All of these biological treatments use certain plants and microorganisms to remediate metals through either adsorption, absorption, or concentration of contaminating metal ions. For example, in bioaccumulation, plants or microorganisms actively take up and accumulate metals from contaminated surroundings.

In phytoremediation, specific plants that have developed the ability to selectively remove metal ions from soil are used. Such plants include certain "hyperaccumulator" species such as the alpine pennycrass plant, which is capable of accumulating metals at levels of 260 times greater than most plants before showing toxicity symptoms. Most hyperaccumulator plants, however, are very slow growing and have specific growth requirements. Some of these growth requirements are not conducive to the use of these plants at sites or in situations where metal recovery or remediation is needed. Furthermore, there are very few plant species known or available for recovery or remediation use. Therefore, given the persistent and high incidence of metal contamination at environmental and waste sites (~75% of Superfund Sites contain metal ions as a form of contamination, U.S. EPA, 1996), more efficient methods and approaches for removing heavy metals from contaminated sources are still needed.

More recently, in an attempt to meet these needs, biotechnological approaches have been employed as an alternative strategy to metal recovery and remediation. Included in these biotechnology approaches are the use of tobacco plants that have been manipulated to express metallothionein genes (Maiti et al., 1991). Metallothioneins (MTs) are small metal binding proteins ubiquitously distributed throughout the animal kingdom. They have high metal binding affinities and are believed to be important in controlling the intracellular levels of free metal ions. However, little else is known about their function or biological purpose. MTs were first discovered in 1957 in horse tissue. Since then, they have been identified in species ranging from fungi and shellfish to mice and humans.

The structural features of MTs include a high cysteine composition and lack of aromatic amino acids. The cysteine residues are responsible for the protein's high affinity metal ion binding capabilities. In general, prior art MTs have a high degree of amino acid sequence similarity. However, the proteins or known gene sequences encoding the prior art proteins have been used primarily in either the research setting or in disease treatment methodologies.

Accordingly, one of the objects of the present invention is to provide novel metal binding proteins and associated methods for their production. This technology would allow for the efficient, cost effective, safe and simple removal of heavy metals from environmental waste or other materials contaminated with heavy metal.

INVENTION SUMMARY

Prior art metallothionein (MT) proteins are generally about 60–68 amino acid residues in size and have a high degree of sequence conservation among the different species. Whereas this high degree of sequence conservation and similarity contributed greatly to the ease of discovery of those MT genes, the novel metal binding proteins of the present invention differ substantially in sequence and were, therefore, much more difficult and required greater perseverance to obtain.

Unlike known prior art MTs, MTs from brine shrimp (Artemia) are much smaller in size (about 48 amino acid residues) and have distinctly unique amino acid and DNA sequences. As a result of these divergences in sequence from prior art MTs, prior to the present invention, the novel metal binding proteins of the present invention were extremely difficult to obtain and the nucleic acid sequences encoding these novel metal binding proteins unknown. The novel metal binding proteins of the present invention are capable of high capacity and high affinity metal binding. This makes them particularly suitable for use in pollution control, metal recycling, metal mining and other metal recovery and metal remediation technologies.

These and other objects are achieved by the compositions and methods of the present invention which provide for the efficient and reliable sequestration of heavy metals from a variety of sources. The novel metal binding proteins of the present invention can be expressed and produced easily for purposes such as metal remediation, metal recycling, metal mining or other types of processes where binding of one or more heavy metals is desired.

In accordance with the teachings of the present invention, novel metal binding proteins are provided. The invention includes at least one substantially purified metal binding protein having an amino acid sequence analogous to at least one metal binding protein sequence from brine shrimp (Artemia). A substantially purified metal binding protein can include an amino acid sequence such as:

[SEQ ID NO:2]
MET ASP CYS CYS LYS ASP GLY CYS THR CYS ALA PRO

ASP CYS LYS CYS ALA LYS ASP CYS LYS CYS CYS LYS

GLY CYS GLU CYS LYS SER ASP PRO GLU CYS LYS CYS

GLU LYS ASP CYS SER CYS ASP SER CYS GLY CYS HIS

STOP;

[SEQ ID NO:4]
MET ASP CYS CYS LYS ASP GLY CYS THR CYS ALA PRO

ASP CYS LYS CYS ALA LYS ASP CYS LYS CYS;

and sequences incorporating one or more conservative amino acid substitutions of SEQ ID NO: 2 or SEQ ID NO:4. It should be noted that while the present invention will be discussed in the context of metal recovery and metal remediation, the present invention is readily applicable to many other uses where removal, recovery or simply binding of heavy metals is desired.

The metal binding proteins of the present invention also include a family of metal binding proteins having multiple isomeric forms. Accordingly, the family of metal binding proteins includes at least 5 isomeric forms of metal binding proteins. Any and all of these metal binding protein isomers are suitable for use in removal or recovery of heavy metals. The "isomers" of the present invention have the requisite structural features that classify them as metal binding proteins. These features include their high cysteine content, which confers their metal binding capacity. Therefore, the metal binding proteins of the present invention, including their isomeric forms, can be expressed and easily produced for purposes such as metal remediation, metal recycling, metal mining or other types of processes involving metal binding.

The novel metal binding proteins of the present invention also have characteristics that further enhance their use in the methods of the present invention and which further distinguish them from the prior art. These advantageous characteristics also render the novel metal binding proteins and associated methods particularly useful in a wide variety of metal recovery and metal remediation settings. For example, the metal binding proteins are capable of heavy metal binding under a range of conditions such as under moderate to high temperature conditions. Metal binding activity occurs from about 4° C. to about 100° C. Depending on a particular application or operation in which a metal binding protein of the present invention is to be implemented, a particular temperature range may be preferred. Therefore, in accordance with the present invention, the suitable range of temperatures include anywhere from about 4° C. to about 100° C. This range of temperature conditions which is incompatible with some prior art methodologies, renders our substantially purified metal binding proteins more versatile and preferable for use in metal recovery, metal remediation or other processes requiring heavy metal binding. Additionally, the metal binding proteins of the present invention are able to bind metal in a variety of chemical conditions. For example, metal binding activity occurs from about pH 4.0 to about 10.0. Bound metal ion(s) can be disassociated or removed from a metal binding protein of the present invention by lowering the pH to about 1.0. An exemplary method comprises slowly increasing the pH to about 7.0 in the presence of a reducing agent, such as dithiothreitol (DTT) for example. This reestablishes the metal binding activity of the metal binding protein and, therefore, the metal binding proteins can be reused if desired.

In further accordance with the teachings of the present invention, isolated nucleic acids encoding the metal binding proteins are provided. These isolated nucleic acids encode metal binding proteins having amino acid sequence analogous to at least one metal binding protein sequence from a brine shrimp (Artemia). An isolated nucleic acid of the present invention can include a DNA sequence such as:

[SEQ ID NO:1]
5'-ATG GAC TGC TGC AAG AAC GGT TGC ACC TGT GCC CCA

AAT TGC AAA TGT GCC AAA GAC TGC AAA TGC TGC AAA

GGT TGT GAG TGC AAA AGC AAC CCA GAA TGC AAA TGT

GAG AAG AAC TGT TCA TGC AAC TCA TGT GGT TGT CAC

TGA-3'.

Alternatively, an isolated nucleic acid of the present invention can include minimal DNA sequences which are sufficient to allow translation of a functional metal binding protein. A DNA sequence encoding a functional metal binding protein of the present invention need not comprise the entire native metal binding protein gene sequence but can be just those portions or regions of SEQ ID NO:1 that confer binding to heavy metals. For example, the present invention can include a DNA sequence comprising:

[SEQ ID NO:3]
5'-ATG GAC TGC TGC AAG AAC GGT TGC ACC TGT GCC CCA

AAT TGC AAA TGT GCC AAA GAC TGC AAA TGC-3'.

Additionally, the present invention also includes DNA having at least 80% or more sequence identity to a DNA molecule having the sequence of SEQ ID NO:1 or a DNA molecule having the sequence of nucleotide residues 1 to 66 of SEQ ID NO:1.

The isolated nucleic acids of the present invention also include nucleic acids encoding any and all of the isomeric or alternative forms of the metal binding proteins disclosed. Additionally, the isolated nucleic acids of the present invention need not comprise entire coding sequences of an MT isomer, but can include nucleic acid sequences encoding domains or portions of a coding sequence encoding an MT isomer, such as, for example, the functional or metal binding regions of the metal binding protein isomers of the present invention.

In further accordance with the teachings of the present invention, the novel metal binding proteins can be utilized as a naked composition or can be provided in association with a support, substrate, or other delivery system to aid in either the dispersal, handling, packaging or function of the metal binding proteins in metal recovery, metal remediation or metal binding processes as disclosed herein. Therefore, any of the metal binding proteins of the present invention can be coupled to a support such as a membrane or filter through which metal containing fluids are brought into contact.

The present invention is particularly well suited for use in metal recovery, metal remediation or metal recycling processes and methods. These methods include contacting a metal binding protein of the present invention having an amino acid sequence analogous to at least one metal binding protein sequence from brine shrimp (Artemia) with a substrate or material having a concentration of at least one heavy metal in order to bind the metal to the metal binding protein; and then separating the bound metal from the substrate or material.

For example, the methods of the present invention are useful in connection with the treatment of any substance having a concentration of at least one heavy metal. As will be appreciated by those skilled in the art, such heavy metal containing substances can be any environmental or industrial material such as ground water, drinking water, contaminated soil, waste, or the like, containing a concentration of metal. Similarly, the methods of the present invention are equally useful in treating industrial or municipal wastes containing metals that are desirable to remove. This broad utility makes the compositions and associated methods of the present invention particularly useful in a wide variety of circumstances.

In further accordance with the novel teachings of the present invention, expression systems producing the novel metal binding proteins of the present invention are provided. These novel metal binding proteins produced by the disclosed expression systems include the metal binding proteins having amino acid sequences analogous to at least one binding protein sequence from a brine shrimp (Artemia), as previously discussed. These expression systems include systems for the production or manufacturing of these compositions which can function in larger scale commercial or industrial plants, as well as in smaller scale, site-specific applications. Also included within the teachings of the present invention are expression systems of live or living production entities such as modified organisms and host cells. These include transgenic plants, transgenic animals and bacteria, and other modified organisms which have been genetically engineered to produce the novel metal binding proteins of the present invention.

Accordingly, the present invention provides unique, relatively small metal binding proteins having unique properties and sequences distinct from those of known prior art metal binding proteins. Furthermore, the novel metal binding proteins of the present invention retain high binding affinity for heavy metals in a variety of conditions, making them particularly useful in situations where removal or recovery of heavy metals from a substrate or any metal containing or metal contaminated source is desired. The novel metal binding proteins and the associated methods of the present invention provide for the efficient, cost effective, and safe removal and recovery of heavy metals from a wide variety of substrates.

The following Detailed Description provides additional enabling disclosure of the present invention and will make apparent to those skilled in the art additional features and advantages thereof.

DETAILED DESCRIPTION OF THE PREFERRED EMBODIMENTS

Figure 1:
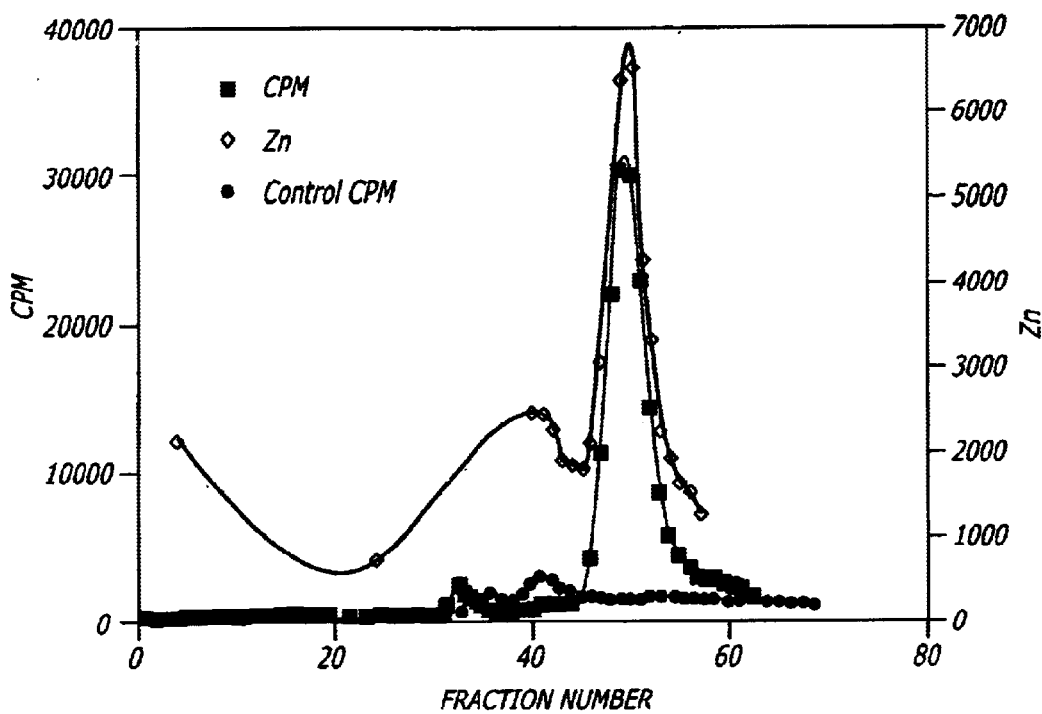
FIG. 1 is an elution profile of exemplary metal binding proteins of the present invention illustrating co-elution of metal binding proteins with the heavy metal, zinc.

Known metal binding proteins (MTs) that have been isolated from various species such as humans, rodents, bacteria, crabs, chickens, etc . . . and are known to have very similar structural characteristics such as similar size (~6.0–6.8 kDa), high amino acid sequence conservation, and a high percentage of cysteine residues in the proteins' total amino acid compositions. It is the cysteine composition of these known MTs that accounts for the protein's binding affinity for heavy metals such as zinc, copper, cadmium, mercury, cobalt, lead, nickel, platinum, silver and gold.

The novel metal binding proteins of the present invention are distinct from all other known MTs because the proteins of the present invention have uniquely different amino acid sequences and DNA sequences. Plus, the proteins of the present invention are much smaller in size when compared to known MTs from other species. Yet, in spite of these differences, the proteins of the present invention retain the ability to bind metals with unexpectedly high affinities. This unusual sequence divergence also made the novel metal binding proteins of the present invention much more difficult to isolate and characterize compared to prior art MTs. For example, the novel metal binding proteins of the present invention are particularly useful in the efficient and cost effective removal of heavy metals from industrial, municipal, and environmental waste. This use of these metal binding proteins for metal remediation is of particular value for pollution control and is particularly applicable to the removal of heavy metals from ground water, contaminated soil, drinking water or any material having heavy metal contamination.

Alternatively, the novel metal binding proteins of the present invention are also very useful in the recovery of metals, particularly precious metals. For example, the metal binding proteins of the present invention can be used in metal mining processes for the isolation and removal of precious metals such as gold, platinum and silver. Doing so eliminates the need to use other toxic metals such as mercury in the final stages of metal purification from ore. These same novel techniques can be utilized to recover such metals from industrial or municipal waste. With the ever increasing use of disposable and other electronic devices, such waste sources are increasingly full of such metals, making recovery a worthwhile endeavor.

In either situation, due to the smaller size of these proteins and the uniquely specific sequence information provided herein, the novel metal binding proteins of the present invention can be isolated easily and efficiently from natural sources or synthetically produced as disclosed herein for use in metal recovery, metal mining, metal recycling, metal remediation, pollution control or any process including metal sequestering. Therefore, the novel metal binding proteins and associated methods of the present invention provide a versatile, easily produced, efficient and reliable resource for use in any process having a metal binding aspect.

The novel metal binding proteins of the present invention were first isolated from brine shrimp (Artemia). They are a family of metal binding proteins which are referred to as "isomers". Analysis of these proteins' unique amino acid compositions showed each isoform to be essentially equivalent. At least five individual isoforms have been identified in accordance with the teachings of the present invention. Unlike MTs from other organisms which share a high degree of sequence homology or similarity, the novel metal binding proteins of the present invention have unexpectedly different structural characteristics but possess a high degree of sequence homology to one another. These distinct sequence characteristics of these proteins of the present invention prevented their earlier isolation and characterization.

After numerous unsuccessful attempts at isolating a gene encoding brine shrimp MT using conventional approaches based upon prior art teachings and MT sequence information, the following techniques were utilized to provide nucleic acid sequence encoding a novel metal binding protein of the present invention. First, a sample of metal binding protein from brine shrimp (Artemia) was isolated and purified. N-terminal amino acid sequence analysis was performed on this metal binding protein-containing sample. This amino acid sequence analysis indicated that the position of the first six cysteine residues of the target brine shrimp (Artemia) metal binding protein was conserved when compared to equine and human MTs, indicating the importance of these amino acid residues in the protein's metal binding function.

Using this N-terminal amino acid sequence information, oligonucleotide primers corresponding to the N-terminal amino acid sequence were constructed as known in the art. These oligonucleotide primers were used to PCR amplify potential candidates for a MT gene sequence encoding at least one of the target metal binding proteins from brine shrimp (Artemia). The PCR product was purified using QiaPrep spin columns (Qiagen, Inc.) and cloned into the TA cloning vector CR2.1 (In Vitrogen) using the manufactures' protocol. Electrocompetent E.coli (Sure Shot cells from InVitrogen) were transformed with the recombinant vector and plated onto LB agar plates containing ampicillin (100 µg/ml) and 1% glucose. The plates were placed at 37° C. overnight. Individual colonies were picked and used to inoculate 5 ml of LB broth supplemented with ampicillin and 1% glucose. The cultures were incubated overnight in a rotary incubator at 37° C. Plasmid was isolate from 2 ml of the cell suspension using QiaPrep spin columns as per the manufacture's protocol (Qiagen). The plamsid was then sequenced on a Li Cor 4200L using the M13 universal forward and reverse primers. Once verified and determined to be a sequence encoding a metal binding protein, the brine shrimp MT gene was subcloned into the bacterial expression vector pTMZ. Based upon the identified MT encoding sequence, the amino acid sequence of the first novel metal binding proteins of the present invention was determined. FIG. 1 details an exemplary elution profile utilizing an exemplary metal binding protein of the present invention. This profile was obtained utilizing the following exemplary protocol.

E.Coli (Strain ER 2566) were transformed with a plasmid expression vector containing the MT gene sequence [SEQ ID NO: 1] in (pTMZ). Bacteria were grown in LB broth containing 1% glucose at 37° C. to an $A_{600}$ of 0.60. The bacterial cells were collected and resuspended in LB broth containing 0.1% glucose and incubated for 45 minutes at the same temperature. Isopropyl b-D-thiogalactopyranoside (IPTG) was added to a final concentration of 0.1 mM. The bacterial cells were incubated for about 16 hours. Non-transformed bacteria were used as controls. The cells were collected by centrifugation and sonicated in 10 mM Tris, pH 8.0, 5 mM DTT and 0.5 mM PMSF. The homogenate was centrifuged at 150,000×g for 1 hour at 4° C. The supernatant was collected and incubated with 2 µCi of $^{109}Cd$ at room temperature. The radiolabeled supernatant was then applied to a G-50 molecular exclusion column and eluted with 50 mM Tris, pH 8.0. Five ml fractions were collected and assayed for radioactivity (CPM) and zinc (PPB), the zinc being an endogenous metal that associates with the exogenous metal binding protein expressed by the transformed bacteria. Each fraction eluting from the column was assayed for Zn by ICPMS(Inductively Coupled Plasma Mass Spectroscopy). The DNA sequence that encodes a functional metal binding protein, such as [SEQ ID NO: 3], may also be utilized, as provided and disclosed by the teachings of the present invention.

Therefore, the present invention provides substantially purified metal binding proteins having amino acid sequence that are analogous to at least one metal binding protein sequence from a brine shrimp (Artemia). The term "substantially purified", as used herein, refers to nucleic acids, amino acids or proteins that have been removed from their natural environment, isolated or separated and are at least 60% free, preferably 75% free, to 90% or more free from other components with which they are naturally associated.

A substantially purified metal binding protein in accordance with the teachings of the present invention has an amino acid sequence analogous to:

```
                                              [SEQ ID NO:2]
MET ASP CYS CYS LYS ASP GLY CYS THR CYS ALA PRO

ASP CYS LYS CYS ALA LYS ASP CYS LYS CYS CYS LYS

GLY CYS GLU CYS LYS SER ASP PRO GLU CYS LYS CYS

GLU LYS ASP CYS SER CYS ASP SER CYS GLY CYS HIS

STOP.
```

Also within the scope of the present invention are substantially purified metal binding proteins that are variants of the sequence of the above SEQ ID NO: 2 that preserve the protein's metal binding affinity. In particular, conservative amino acid substitutions within the scope of the present can include any of the following: (1) any substitution of isoleucine for leucine or valine, leucine for isoleucine, and valine for leucine or isoleucine; (2) any substitution of aspartic acid for glutamic acid and of glutamic acid for aspartic acid; (3) any substitution of glutamine for asparagine and of asparagine for glutamine; and (4) any substitution of serine for threonine and of threonine for serine.

A "conservative amino acid substitution" as used herein, refers to alteration of an amino acid sequence by substituting an amino acid having similar structural or chemical properties. Those skilled in the art can determine which amino acid residues may be substituted, inserted or altered without the metal binding properties of the proteins of the present invention.

Other substitutions can also be considered conservative, depending upon the environment of the particular amino acid. For example, glycine (G) and alanine (A) can be interchangeable, as can be alanine and valine (V). Methionine (M), which is relatively hydrophobic, can be interchanged frequently with leucine and isoleucine, and sometimes with valine. Lysine (K) and arginine (R) are interchangeable in locations in which the significant feature of the amino acid residue is its charge and the different pK's of these two amino acid residues and where their different sizes are not significant. Still other changes can be considered "conservative" in particular environments, as known in the art.

For example, if an amino acid on the surface of a protein is not involved in a hydrogen bond or salt bridge interaction with another molecule, such as another protein subunit or a ligand bound by the protein, negatively charged amino acids such as glutamic acid and aspartic acid can be substituted with positively charged amino acids such as lysine or arginine and vice versa. Histidine (H), which is more weakly basic than arginine or lysine, and is partially charged at neutral pH, can sometimes be substituted for these more basic amino acids as well. Additionally, the amides glutamine (Q) and asparagine (N) can sometimes be substituted for their carboxylic acid homologues, glutamic acid and aspartic acid.

The novel metal binding proteins of the present invention, and their associated methods of production and use, are a family of metal binding proteins having multiple isomeric forms. As a result, the present invention includes at least 5 isomeric forms of metal binding proteins suitable for use in removal or recovery of heavy metals. An isomer is one of two or more compounds that have the same chemical composition but differ in structural form. The "isomers" of the present invention have the requisite structural features that classify them as metal binding proteins. These features include their high cysteine content, which confers their metal binding capacity. The isomers differ by two or more amino acid residues, resulting in different pI's for the individual isomer. This pI difference allows easy separation and characterization of the isoforms. Therefore, the metal binding proteins of the present invention can be expressed and produced efficiently and with ease.

In addition to their metal binding properties, the metal binding proteins of the present invention also exhibit features which render them particularly useful in a wide variety of metal recovery and metal remediation settings. For example, these novel metal binding proteins are capable of heavy metal binding under a range of conditions such as under moderate to high temperature conditions. The novel metal binding proteins are capable of heavy metal binding at room temperature and therefore particularly ideal for many applications. The novel metal binding proteins are also capable of heavy metal binding within a wide temperature range such as, for example, a temperature range of about 4° C. to about 100° C. Those skilled in the art will appreciate that depending on a particular application or operation in which the metal binding proteins are to be utilized, a particular temperature range may be preferred for practical or economic reasons. For example, it may be more practical to use the metal binding proteins "on-site" or at the location of an environmental contamination (which would dictate that particular temperature range that can be obtained within available costs). On the other hand, more effective metal extraction on certain substrates may be achieved by use of the metal binding proteins of the present invention under relatively high temperature conditions. Therefore, in accordance with the teachings of the present invention, a suitable range of temperatures for practicing the present invention includes a range of about 4° C. to about 100° C. This range of temperature conditions makes the metal binding proteins of the present invention more versatile and useful.

In further accordance with the teachings of the present invention, the metal binding proteins can be utilized as a naked composition or in association with a substrate or dispersal means to aid in either the dispersal, handling, packaging or function of the metal binding protein in metal recovery, metal remediation or metal binding processes. Such metal binding proteins are particularly useful in metal recovery, metal remediation and metal binding processes because they can be more easily and safely used as compared to other methodologies, such as chemical extraction, which exposes the user to toxic or other potentially dangerous types of chemicals.

A variety of supports to aid in the handling or dispersal of the novel metal binding proteins can be used and include solid supports, matrices, membranes, semi-permeable membranes, powders, devices, apparatuses, liquids, formulations, and other materials. It should be noted, that an additional characteristic feature of the novel metal binding proteins are that they are also capable of reversible heavy metal binding. For example, bound metals can be eluted off or away from the metal binding proteins using acidic conditions or by instantaneous exchange reactions or inorganic chelators. For example, during incubation of a metal binding protein with radioactive Cd, the $^{109}$Cd metal exchanges for endogenous metal bound to the metal binding protein. At about pH 1.0, the metal is released from the protein. Bringing the pH of the solution up to about pH 8.0 regenerates the metal binding activity of the protein. Therefore, due to the reversible binding characteristics of the novel metal binding proteins, the present invention also provides compositions, formulations, powders, liquids, devices or apparatuses comprising the substantially purified metal binding proteins which can be utilized more than once, or which can be reused.

Turning now to an exemplary discussion of the genetic engineering of the novel metal binding proteins of the present invention, a nucleotide sequence for one of the isoforms of a metal binding protein from a brine shrimp (Artemia) was identified, as discussed above. Generally, the isolation process comprises: (1) preparation of one or more sample(s) containing nucleic acids from brine shrimp (Artemia); (2) isolation of total RNA from Artemia; (3) preparation of cDNA from the total RNA; (4) amplification of metal binding protein gene sequences; and (5) cloning, sequencing and verification of an isolated nucleic acid sequence as a metal binding protein gene (MT) from brine shrimp (Artemia).

The above procedure yielded the entire coding sequence for one of the metal binding protein genes, MT. This sequence is:

[SEQ ID NO:1]
5'-ATG GAC TGC TGC AAG AAC GGT GCC ACC TGT GCC

CCA AAT TGC AAA TGT GCC AAA GAC TGC AAA TGC TGC

AAA GGT TGT GAG TGC AAA AGC AAC CCA GAA TGC AAA

TGT GAG AAG AAC TGT TCA TGC AAC TCA TGT GGT TGT

CAC TGA-3'.

Therefore, the invention also provides one or more nucleic acid sequences encoding a substantially purified metal binding protein having amino acid sequence analogous to at least one metal binding protein sequence from brine shrimp (Artemia). The nucleic acid sequences include the sequence of SEQ ID NO: 1; a sequence complementary to SEQ ID NO: 1; or a sequence complementary to SEQ ID NO: 1 with no greater than about a 15% mismatch under stringent conditions. Preferably, the degree of mismatch is no greater than about 5%; most preferably the mismatch is no greater than about 2%.

Alternatively, an isolated nucleic acid can comprise the minimal DNA sequences sufficient to allow translation of a functional metal binding protein. A functional metal binding protein need not be the entire native metal binding protein but can be just those portions or regions of SEQ ID NO:1 that encodes a protein capable of binding to heavy metals. Therefore, the invention also includes isolated nucleic acids including DNA having at least 80% sequence identity to a DNA molecule having the sequence of nucleotide residues 1 to 66 of SEQ ID NO: 1.

Also within the present invention is a nucleic acid sequence encoding any one of the novel metal binding proteins of the present invention. Such novel metal binding proteins can have molecular weight of about 5,800 daltons and are able to bind with high affinity to heavy metal ions such as zinc, copper, cadmium, mercury, cobalt, lead, nickel, platinum, silver and gold, etc . . . The novel metal binding proteins include therein an amino acid sequence selected from the group consisting of: SEQ ID NO: 2 and sequences incorporating one or more conservative amino acid substitutions thereof wherein the conservative amino acid substitutions are any of the following: (1) any of isoleucine, leucine and valine for any other of these amino acids; (2) aspartic acid for glutamic acid and vice versa; (3) glutamine for asparagine and vice versa; and (4) serine for threonine and vice versa. Alternative nucleic acid sequences can be determined using the standard genetic code; the alternative codons are readily determinable for each amino acid in this sequence.

It should be noted, that while the isolated nucleic acids provided herein can be used to produce or express novel metal binding proteins, they are also particularly useful for isolation and identification of additional metal binding protein genes encoding the novel metal binding proteins of the present invention. For example, using the strategy, exemplary methods and nucleic acid sequences provided herein, DNA sequences encoding any of the metal binding protein isomers can be obtained. Therefore, the present invention includes nucleic acids encoding any and all of the isomeric or alternative forms of the metal binding proteins of the present invention. Additionally, isolated nucleic acids need not comprise entire coding sequences of an MT isomer, but include nucleic acid sequences encoding domains or portions of a coding sequence encoding an MT isomer, such as the functional or metal binding regions of the metal binding protein isomers of the present invention.

Construction and isolation of nucleic acid sequences according to the present invention can be accomplished by techniques well known in the art, including solid-phase nucleotide synthesis, the polymerase chain reaction (PCR) technique, reverse transcription of DNA from RNA, the use of DNA polymerases and ligases, and other techniques. Using an amino acid sequence encoding a metal binding protein or portion of a metal binding protein of the present invention, the corresponding nucleic acid sequence can be constructed according to the genetic code as known in the art.

Another aspect of the invention is a vector comprising a nucleic acid sequence according to the present invention operatively linked to at least one control sequence that controls the expression or regulation of the nucleic acid sequence. Such control sequences are well known in the art and include operators, promoters, enhancers, promoter-proximal elements and replication origins. The techniques of vector construction, including cloning, ligation, gap-filling, the use of the polymerase chain reaction (PCR) procedure, solid-state oligonucleotide synthesis, and other techniques, are all well known in the art and need not be described further here. The vectors of the present invention are particularly useful in producing the novel metal binding proteins either by modified organisms, host cells or other types of expression systems.

Therefore, another aspect of the present invention is a host cell or modified organism transfected with a vector according to the present invention. Among the host cells that can be used are bacteria, plants, algae, shrimp, fish, or any organism suitable for genetic modification to produce a novel metal binding protein of the present invention.

Transfection, also known as transformation, is performed using standard techniques appropriate to the host cell or organism used. Such techniques are described, for example, in Sambrook et al., supra.

Turning now to uses for the novel metal binding proteins of the present invention. These include pollution control applications of the metal binding proteins such as metal remediation, pollution control, metal recycling or metal mining. For example, the novel metal binding proteins can be used to reduce the concentration of heavy metals in an environmental substance. The substance can be a fluid, such as ground water, sludge, waste-water and the like. Additionally, the novel metal binding proteins can be incorporated into one or more compositions or devices used for pollution control. For example, the novel metal binding proteins can be applied on site in the form of a flocculent or powder, or can be used in treatment plants as part of a membrane filtration or other type of solid support device used for removal of heavy metal from a contaminated substrate.

The novel metal binding proteins used in these metal binding processes can be provided as a product purified from its natural source or can be produced by bioengineering techniques. For example, the novel metal binding proteins can be produced by transgenic or modified organisms. Modified organisms include transgenic animals, bacteria or plants. For example, a modified plant can be a transgenic tobacco plant whose genome has been genetically altered to express one or more novel metal binding protein of the present invention. A modified organism can also include a plant or biomass that is capable of growing at or within contaminated sites where metal remediation is desired. Extraction of metal contaminants by the modified organisms also concentrates the toxic metals from the contaminated site. This provides the additional advantage of converting the heavy metals to a smaller quantity as well as providing final product that is more easily and safely handled for disposal or further processing.

Methods for reducing the concentration of heavy metals in a substrate include contacting a novel metal binding protein of the present invention with a substrate having heavy metals. For example, a metal binding protein having an amino acid sequence analogous to at least one metal binding protein sequence from brine shrimp (Artemia) can be contacted with a substance having a concentration of at least one heavy metal to bind the heavy metal to the metal binding protein. Subsequently, the bound heavy metal can be separated from the substrate, reducing the concentration of heavy metals in the original substrate.

As mentioned previously, an additional advantageous feature of the novel metal binding proteins of the present invention include their ability to release bound heavy metals using acid extraction, inorganic chelators, and/or exchange reaction technologies. This allows the user, if desired, to elute bound heavy metals off the novel metal binding proteins. Once the heavy metals are eluted off the metal binding proteins of the present invention, the metal binding proteins can be regenerated (or recycled) for additional uses in metal extraction. Therefore, the invention also provides methods for reducing the concentration of heavy metals in a substrate using reusable compositions, devices and apparatuses comprising the novel metal binding proteins.

Metal binding proteins of the present invention, when used in methods for reducing the concentration of a metal ion in a substrate can be provided in such a way as is appropriate for the particular use, situation, mode of administration or environment in which the metal binding proteins are to be used. For example, when used in metal remediation, or in pollution control, the metal binding proteins can be coupled to a support, such as a powder and used, for example, as a flocculent to provide a convenient and efficient means of dispersing the metal binding proteins.

Alternatively, the metal binding proteins can be provided coupled to a membrane, a semi-permeable membrane, a filter, or any other means appropriate for allowing sufficient exposure of the novel metal binding proteins to the heavy metal containing substrate so as to bind or sequester the heavy metals from the substrate. A membrane or filter comprising the novel metal binding proteins provides a particularly efficient means of treating ground water or waste water, as contaminated water can be purified by passage through the membrane or filter without further clean up as is required in chemical extraction processes. Coupling the novel metal binding proteins to a support or supporting matrix also affords easier handling of the metal binding proteins especially when used in large scale or industrial applications.

Use of the metal binding proteins of the present invention are not limited only to those methods where removal of heavy metals is desired, but can also include methods where recovery or concentration of heavy metals in a substance is to be achieved. For example, the novel metal binding proteins can be used for metal-mining, such as in the recovery of precious metals including gold, platinum and silver, or can be used to concentrate metals in hazardous conditions, such as hazardous waste containing radioactive metals. Such hazardous metal waste can result either from numerous research, commercial or industrial uses.

Use of the novel metal binding proteins in concentrating radioactive metals from waste also reduces the amount or quantity of hazardous waste to be disposed of. Reducing the quantity of hazardous metal waste also reduces the level of radioactivity to which certain individuals are exposed. For example, individuals working with or near materials containing hazardous heavy metals will have a reduced overall exposure to radioactive metal waste due to the decreased quantity or volume of radioactive waste requiring human handling. This provides an additional advantageous aspect of using the novel metal binding proteins of the present invention in metal binding processes.

Methods for reducing the concentration of heavy metals in a substance include producing the novel metal binding proteins in a modified organism. Modified organisms include, for example, transgenic organisms or transgenic hosts. For example, hosts or organisms such as shrimp, plants, bacteria, or algae can be modified using molecular and genetic engineering techniques well known in the art. Using these techniques, which are described for example, in Sambrook et al., *Molecular Cloning: A Laboratory Manual* (New York: Cold Spring Harbor Press, 2001); Ausubel et al. *Current Protocols in Molecular Biology* (Wiley lnterscience Publishers, 1995); US Dept Commerce/NOAA/NMFS/NWFSC Molecular Biology Protocols (URL:http://research.nwfsc.noaa.gov/protocols.html); or Protocols Online (URL:www.protocol-online.net/molbio/index.htm), organisms whose genome are modified so as to result in expression of a novel metal binding protein are provided. Novel metal binding proteins of the present invention include metal binding proteins having an amino acid sequence analogous to at least one metal binding protein sequence from a brine shrimp (Artemia). Modified organisms can be made and used to produce these novel metal binding proteins, and the novel metal binding proteins useful in the methods provided herein.

A modified organism producing a novel metal binding protein of the present invention includes a modified organism producing at least one metal binding protein having an amino acid sequence substantially similar to a metal binding protein from a brine shrimp (Artemia). A modified organism also includes an organism producing a metal binding protein having an amino acid sequence substantially similar to SEQ ID NO: 2 or conservative amino acid substitutions thereof.

Alternatively, production or expression of the novel metal binding proteins of the present invention from modified organisms is not limited to genomic expression of the novel metal binding proteins, but also includes epigenetic expression of the novel metal binding proteins from the modified organisms. Methods and techniques for obtaining epigenetic expression from a modified organism include, for example, adenoviral, adeno-associated viral, plasmid and transient expression techniques which are known in the art.

When dealing with genes from eukaryotic organisms, it is preferred to use cDNA, because the natural gene typically contains intervening sequences or introns that are not translated. Alternatively, since the amino acid sequence is known, a synthetic gene encoding the protein to be sorted can be constructed by standard solid-phase oligodeoxyribonucleotide synthesis methods, such as the phosphotriester or phosphite triester methods. The sequence of the synthetic gene is determined by the genetic code, by which each naturally occurring amino acid is specified by one or more codons. Additionally, for isomers or other variant metal binding proteins, if a portion of the isomer's protein sequence is known, but the gene or messenger RNA has not been isolated, the amino acid sequence can be used to construct a degenerate set of probes according to the known degeneracy of the genetic code. General aspects of cloning are described, for example, in Sambrook et al., supra; in B. Perbal, "A Practical Guide to Molecular Cloning" (2d ed., John Wiley & Sons, New York 1988), in Berger &. Kimmel, "Guide to Molecular Cloning Techniques" (Methods in Enzymology, vol. 152, Academic Press, Inc., San Diego, 1987), and in D. V. Goeddel, ed., "Gene Expression Technology" (Methods in Enzymology, vol. 185, Academic Press, Inc., San Diego, 1991).

The present invention includes methods for producing the novel metal binding proteins of the present invention. For example, a method for producing a metal binding protein having an amino acid sequence analogous to at least one metal binding protein from a brine shrimp (Artemia) includes providing an expression system, producing a novel metal binding protein using the expression system and purifying or isolating the novel metal binding proteins to obtain a metal binding protein of the present invention.

Expression systems can be systems such as traditional manufacturing plants. For example, organisms such as brine shrimp can be grown and the novel metal binding proteins of the present invention purified or extracted from the tissues of the brine shrimp. Alternatively, biomanufacturing systems using genetically engineered organisms (produced as described herein) capable of producing the novel metal binding proteins can be used to produce the novel metal binding proteins. For example, bacteria containing a metal binding protein expression vector can be cultured on large or small scale (depending on the particular need). The novel metal binding proteins can then be purified from the bacterial broth and used in metal binding processes.

Therefore, a novel metal binding protein of the present invention can be produced by expression of a nucleic acid sequence encoding a metal binding protein in a modified organism or host cell. Such nucleic acid sequence includes, for example, a MT gene such as [SEQ ID NO: 1] or a sequence encoding a fragment or functional metal binding domain of a MT gene. The isolation of nucleic acid sequences or segments encoding metal binding proteins of the present invention are described above. Once isolated, these nucleic acid sequences are then incorporated into an expression vector. This expression vector is then use to modify an organism for producing the novel metal binding proteins of the present invention. Expression or production is typically under the control of various control elements associated with the vector construct. Such elements can include promoters, operators, enhancers and negative regulatory elements which allow the user to regulate production of the novel metal binding proteins of the present invention. The conditions required for expression of cloned protein sequences in modified organisms are well known in the art.

The expressed metal binding proteins are then purified using standard techniques. Techniques for purification of cloned proteins are well known in the art and need not be detailed further here. One particularly suitable method of purification is affinity chromatography employing an immobilized antibody to a metal binding protein. Other protein purification methods include chromatography on ion-exchange resins, gel electrophoresis, isoelectric focusing, and gel filtration, among others. Alternatively, the metal binding proteins of the present invention can be purified following their expression from modified organisms by methods such as precipitation with reagents (e.g. ammonium sulfate or protamine sulfate as well as other methods known in the art).

A further understanding of the present invention will be accorded to those skilled in the art from a consideration of the following non-limiting Examples. These examples illustrate the cloning and expression of exemplary metal binding proteins in accordance with the teachings of the present invention that are useful in the removal or recovery of heavy metals from substrates.

It is emphasized that these examples are illustrative of the principles and teachings of the present invention and are not intended to limit the scope of the invention to exemplary brine shrimp (Artemia) metal binding proteins alone.

EXAMPLE 1

In accordance to the teachings of the present invention, the following exemplary protocols illustrate methods useful in the production, purification and analysis of the novel metal binding proteins of the present invention.

Sample Preparation

As a preliminary step in the isolation of the novel metal binding proteins, Artemia brine shrimp were grown in artificial seawater (AS) (422.7 mM NaCl, 7.24 mM KCL, 22.58 mM $MgCl_2$-$6H_2O$, 25.52 mM $MgSO_4$-$7H_2O$, 1.33 mM $CaCl_2$-$2H_2O$ and 0.476 mM $NaHCO_3$). Artemia cysts (2.5 g) were incubated for 48 hours in 250 ml of AS supplemented w/antibiotics at 30° C., rotating at 125 rpm. After 24 hrs, phototropic Artemia were collected, cultured for an additional 24 hrs and then collected by cloth filtration. The shrimp were weighed and if not used immediately, stored at −80° C.

The Artemia were then homogenized in homogenization buffer (HB) (10 mM Tris-HCl (pH 8.0), 0.1 mM DTT, 0.5 mM PMSF and 10 µg/ml Soybean Trypsin Inhibitor) and resuspended in HB at 4 ml/gm wet wt of shrimp. The homogenate was passed through a Yamato LH-21 homogenizer three times at a setting of 800 rpm, filtered through Miracloth (Calbiochem) and the filtrate centrifuged in a Sorvall SA-600 rotor @ 14,300 rpm, 4° C. for 30 min. The lipid layer on top of the supernatant was removed by vacuum aspiration and the lower supernatant layer collected and centrifuged in a Beckman 50.2TI rotor @ 40K rpm, 4° C. for 90 min. Again, the upper lipid layer was removed and the lower supernatant recentrifuged at 150K (150K sup). The 150K sup was then used immediately or stored at −80° C. If used immediately, this product was then subjected to gel filtration as follows. The gel filtration studies verified the novel metal binding proteins' ability to bind to heavy metals.

Gel Filtration Studies

The 150K sup was centrifuged in a Sorvall SA-600 rotor at 8,500 rpm and 4° C. for 30 min. The resulting supernatant was then filtered through a HPLC certified 0.45 micron LC13 acrodisc filter (Gelman Sciences). A 20 ml aliquot of filtered 150K sup was incubated at 4° C. for 20 min with 2 $\mu$l of $^{109}$Cd (0.066 $\mu$Ci) to radiolabel the metal binding proteins. The sample was then applied to a Sephadex G-50 molecular weight exclusion column (2.6×94 cm) previously equilibrated with 50 mM Tris-HCl (pH 8.0) saturated with $N_2$. One molar DTT (2 $\mu$l) was added to fractions 60–100 prior to sample loading in order to maintain reducing conditions in the fractions containing the low molecular weight metal binding proteins. The column was eluted with 50 mM Tris (pH 8.0) at a flow rate of 20 ml/hr while monitoring the eluate at 280 nm. During the elution period, the buffer reservoir was continually purged with $N_2$. Samples used for amino acid analysis were not radiolabeled.

The $^{109}$Cd content (CPM) of the column fractions was determined with an Auto-Logic gamma counter (ABBOTT Laboratories). Zinc content was measured by Flame or Furnace Atomic Absorption Spectroscopy and expressed as PPB zinc/fraction. Prior studies indicated that two classes of metal binding proteins were present, one class being a high molecular weight fraction. However, the majority of $^{109}$Cd eluted with a low molecular weight class of zinc containing metal binding protein. As shown in FIG. 1, radioactive metal binding protein had a elution peak corresponding to that for Zinc (roughly, fraction #50). The protein concentration of the Sephadex G-50 fractions was determined with a BCA Total protein assay kit (Pierce) according to manufacturers protocol. The protein concentration of the low molecular weight fractions was determined using the enhanced protocol which has greater sensitivity than the standard protocol. The distinct structural features of the novel metal binding proteins of the present invention were then identified in the following studies.

Metal Binding Protein Characterization Studies

All chromatographic and molecular weight studies were performed to ascertain structural features of the novel metal binding proteins. All protocols used were as described previously in B. Harpham, "Isolation of Metal Binding Proteins From Artemia", Master's Thesis, California State University, Long Beach Library, 1998. Using anion exchange and reverse phase chromatography techniques well known in the art and described, for example, in B. Harpham "Isolation of Metal Binding Proteins From Artemia", supra, metal binding proteins from Artemia were purified and determined to have molecular weights and amino acid sequence length unexpectedly lower than other known metal binding proteins. Under SDS-PAGE conditions, Artemia metal binding proteins have molecular weight of about 5.8 kDa as compared to 6–7 kDa for metal binding proteins from other mammalian species. Protein analysis of Artemia metal binding proteins indicate a sequence length of 48 amino acids. Artemia amino acid sequence was unexpectedly and significantly shorter in length than other known metal binding proteins, which range in length from 60 to 68 amino acid residues.

Due to the unexpectedly distinct structural features of the novel metal binding proteins, attempts at isolating nucleic acid sequences encoding a novel metal binding protein of the present invention using prior methodologies failed. Therefore, an alternative strategy was employed to isolate our MT gene encoding a novel metal binding protein.

EXAMPLE 2

In accordance with the teachings of the present invention, the following teaches an exemplary strategy effective for cloning a novel metal binding protein genes. The cloned metal binding protein gene and its sequence information are particularly useful for expression of metal binding proteins useful in the methods of the present invention.

Prior attempts at cloning and obtaining a gene encoding a brine shrimp (Artemia) metal binding protein had been unsuccessful. Therefore, using protein purification techniques described, for example, in B. Harpham "Isolation of Metal Binding Proteins From Artemia", supra, sequence data was obtained for the N-terminal region of isoforms of Artemia metal binding protein. Sequence data from four of the metal binding protein isoforms indicated identical amino acid sequences through amino acid number ten. Using this sequence information, oligonucleotide primers unique to our novel metal binding proteins were constructed and used to isolate a gene encoding a novel metal binding protein as follows.

Cloning and Sequencing of a Gene Encoding Artemia Metal Binding Protein

Total RNA was isolated from 48 hour nauplii using the RNAzol method. Forty-eight hour nauplii samples were prepared as described above in Example 1. The PolyTract Procedure (Promega, Wis.) was then used to isolate mRNA from the total RNA samples. cDNA was generated from the mRNA using SuperScript and 3' RACE Kit procedures (Cat #18373, Gibco/BRL, WI) and then subjected to the following synthesis reaction.

| cDNA synthesis reaction: | |
| --- | --- |
| Artemia mRNA | 25 $\mu$l (500 ng) |
| DEPC H$_2$O | 30 $\mu$l |
| 10 uM AP | 5 $\mu$l |

The above mixture was incubated for 10 min @ 70° C., then placed on ice for 1–2 min. Volatilized liquid was collected by centrifugation for 10 sec @ 10,000 rpm. The following were then added to the above RNA cocktail to produce a PCR solution:

| | |
| --- | --- |
| 10x PCR Buffer | 10 $\mu$l |
| 25 mM MgCl$_2$ | 10 $\mu$l |
| 10 mM dNTP | 5 $\mu$l |
| 0.1 mM DTT | 10 $\mu$l |

The above resulting PCR solution was then mixed and incubated at 42° C. for 5 min. Five (5) $\mu$l of Superscript II RT was added and the mixture incubated @ 42° C. for 50 min for cDNA synthesis. The reverse transcription reaction was terminated by incubating the solution for 15 min at 70° C. 5 $\mu$l of RNase was then added and the solution incubated for 20 min at 37° C. The final solution containing Artemia cDNA was then stored at −20° C. until used for PCR amplification as described below.

PCR Amplification of Artemia Metal Binding Protein Sequences

The initial PCR Primer Sequences used were as follows:

5' primer (N-terminal side) designated "MT-Not I" [SEQ ID NO:5] consisted of

5'-ACC TAT GCG GCC GCA AAT GGA CTG CTG CAA GAA C-3'

(underlined nucleotides designate the Not I restriction site); and

3' primer (C-terminal side) designated as "dT-Spe I" was:

[SEQ ID NO:6]
5'-GCA CCA ACT AGT GCC TTT TTT TTT TTT TTT A-3';
or

[SEQ ID NO:7]
5'-GCA CCA ACT AGT GCC TTT TTT TTT TTT TTT C-3';
or

[SEQ ID NO:8]
5'-GCA CCA ACT AGT GCC TTT TTT TTT TTT G-3'.

The above 5' and 3' primers were then used in the following amplification cocktail.

| PCR Reaction Cocktail: | |
|---|---|
| 10X PCR Buffer | 5 µl |
| 25 mM MgCl$_2$ | 3 µl |
| 10 mM dNTP | 1 µl |
| 10 µM dT-SpeI | 1 µl |
| 10 µM MT-Not I | 1 µl |

To the above PCR Reaction cocktail, a Gem 50 wax bead was added to the tube and the tube incubated at 80° C. for 2–3 minutes. Upon hardening of the wax at room temp for 10–15 min, the following were layered on top of the hardened wax:

| Sterile H$_2$O | 36.5 µl |
|---|---|
| cDNA mixture | 2 µl |
| Taq Polymerase | 0.5 µl |

This final mixture was then subjected to the following PCR amplification program.
PCR Program:
Initial denaturation for 3 min @ 95° C., followed by 29 cycles of:
94° C. for 1 min
49° C. for 1 min
72° C. for 1 min
72° C. for 10 min
Hold at 4° C.

Once amplified, the PCR product was verified for successful amplification on a 1.2% agarose gel. The PCR product was then purified for subsequent cloning using Qiagen QIAquick Gel Extraction (Qiagen, Calif.), double digested to form compatible ends and the purified using Qiagen QIAquick PCR Purification protocol. The following primers which contain modifying restriction sites incorporated into their sequence were used to subclone the purified PCR product containing brine shrimp Artemia metal binding protein gene sequences.

MT Nco 1 (5' primer containing an Nde I site):
[SEQ ID NO:9]
Nde 1    Nco 1
5'-GCT ACA CAT ATG TCC ATG GAC TGC TGC AAG AAC-3'

MT Sal 1 (3' primer containing Sal 1 site):
[SEQ ID NO:10]
Sal 1
5'-ACG AAC GTC GAC GCC TTT TTT TTT TTT A-3'

Using the Mt Nco I and MT Sal I primers, with an annealing temperature of 72° C. for 1 min, the Artemia MT nucleotide sequence was amplified and then subsequently subcloned into the pGEM3 vector between the vector's Eco RI and Sal I sites. Once subdloned, the cloned metal binding protein gene can then be easily modified or further processed for use in expression, production or other methods requiring use of an isolated nucleic acid encoding a metal binding protein.

The entire coding sequence for MT gene was then determined using a LiCor 4200L DNA sequencer. Sequence comparison studies of the MTgene from Artemia indicate it to have unexpectedly different sequence as compared to other known metal binding protein genes. When Artemia MT gene sequence was aligned with that of Equine and Human MT, homology was observed. The ability of the exemplary metal binding protein of the present invention to bind heavy metals was then confirmed in the following studies.

EXAMPLE 3

The following teaches an exemplary study which can be performed on any of the novel metal binding proteins of the present invention to aid in either the verification of a protein as a metal binding protein or in the identification of a protein as a novel metal binding protein. For example, the metal binding proteins of the present invention are capable of binding heavy metals such as zinc, cadmium and copper. The ability of an isolated protein to bind heavy metals was described and detailed in the disclosed transformation of E. coli with an exemplary MT of the present invention and shown, as indicated in FIG. 1.

As described previously, modified organisms useful for producing the novel metal binding proteins of the present invention can be made following the teachings provided herein. An exemplary modified organism includes a transgenic tobacco plant which is particularly useful in the methods described herein. The following illustrates exemplary methods useful in producing a modified organism of the present invention.

EXAMPLE 4

Transgenic Tobacco Plant

Figure 2:
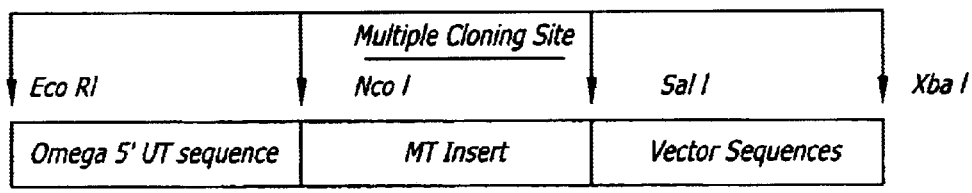
FIG. 2 is a map of an exemplary cloning cassette containing the gene sequence of the metal binding gene, in accordance with the teachings of the present invention.

The cDNA for MT cloned into TOPO.CR2 vector is refered to as pART$_{mt}$. The coding sequence for the MT was cloned into a pUC18 based plasmid containing the omega 5' untranslated region of the TMV coat protein in frame with the multiple cloning site. (See FIG. 2). This was accomplished by amplification of the MT coding sequence from pART$_{mt1}$ using PCR primers containing an Nco I restriction site on the 5' primer and a Sal I site on the 3' primer. The PCR product and vector were each restricted with Nco I and Sal I and purified. The PCR product was then ligated into the vector using T4 DNA ligase. The ligation mixture was used to transform DH5α cells by electroporation. LB media was inoculated with individual colonies and grown overnight. Plasmid was isolated and sequenced to verify the presence and integrity of the MT coding sequence.

The Eco RI/Xba I cassette was removed and cloned into the corresponding sites on the plant expression vector pSS. The pSS vector contains the constitutive CMV promotor and transcription terminator sequence in frame with the multiple cloning site. This insures that ligation of the Eco RI/Xba I cassette into the vector places the MT gene sequence in-frame with the CMV promotor. We refer to the construct as pSSmt. The pSSmt was propagated in DH5α cells, isolated and sequenced to verify the presence and integrity of the MT gene as described above.

MT Expression in Tobacco Leaves

A. tumefaciens were transformed with the cytosolic $pSS_{mt}$ construct by electroporation and grown overnight at 27° C. in YEB medium, pH 7.4, containing antibiotics. The cells were collected and resuspended in induction medium (YEB, pH 5.8, antibiotics and 20 μM Acetosyringone) and grown overnight at 27° C. The next morning the cells were collected by centrifugation and resuspended in infiltration medium (MMA buffer containing antibiotics and 200 μM Acetosyringone) to an $A_{600}$ of 1.5 and incubated at room temperature for 2 hrs. Plant leaves were submerged in the bacterial suspension and placed in a vacuum dessicator. The leaves were infiltrated under a vacuum of 30–40 mbar. The leaves were placed at room temperature for 72 hours then ground to a fine powder in liquid nitrogen and extracted with 10 mM Tris pH=8.0, 0.05 mM DTT, 1 mM PMSF. The solution was clarified by centrifugation at 30,000×g and the supernatant assayed for MT using a $^{109}$Cd metal binding assay. Metal binding activity is clearly evident in the leaves containing the gene for Artemia MT.

| Treatment | Bound Cd (CPM) |
|---|---|
| Buffer | 747 |
| Untreated Leaves | 5052 |
| Infiltrated Leaves I | 12874 |
| Infiltrated Leaves II | 12763 |

Stable Transformation of Tobacco (Nicotiana tabacum)

A suspension of A.tumefaciens transformed with $pSS_{mt}$ were grown as described above. Leaves were cut into small pieces (without the central vein) and transferred into sterile weck glasses containing 50–100 ml of bacterial suspension ($A_{600}$~1.0) and incubated at room temperature for 30 minutes. The leaf pieces were then transferred onto sterile Whatman 3MM filterpaper pre-wetted with sterile water in plastic petri dishes. The dishes were sealed with saran wrap and incubated at 26–28° C. in the dark for two days. The leaf pieces were then washed with sterile water containing antibiotics and transferred onto MS II agar plates. The pieces were incubated at 25° C. for 3–4 weeks with a 16 hr photoperiod. When shoots began to form, the shoots were removed and transferred onto MS III agar plates and incubated at 25° C. with a 16 hr photoperiod until roots began to form. The small plants were transferred into weck glasses containing MS III medium and incubated at 25° C. with a 16 hr photoperiod for about two weeks. The young plants were then planted into soil. Young leaves from the plants were collected and assayed for MT activity as described above to determine the transgenic plants.

In closing it is to be understood that the embodiments of the invention disclosed herein are illustrative of the principals of the invention. Other modifications may be employed which are within the scope of the invention and accordingly, the present invention is not limited to that precisely as shown and described in the present specification.

We claim:

1. An isolated nucleic acid encoding for an amino acid sequence comprising SEQ. ID. NO. 2.

2. An isolated nucleic acid encoding for an amino acid sequence comprising SEQ. ID. NO. 4.

3. An isolated nucleic acid comprising the nucleotide sequence of SEQ. ID. NO. 1 wherein said isolated nucleic acid sequence encodes an Artemia metallothionein (MT) protein.

4. An isolated nucleic acid comprising the nucleotide sequence of SEQ. ID. NO. 3 wherein said isolated nucleic acid sequence encodes a metal binding region of an Artemia MT protein.

5. The isolated nucleic acid according to any one of claims 1 and 2 wherein said isolated nucleic acid is isolated from brine shrimp.

6. The isolated nucleic acid according to claim 5 wherein said brine shrimp is from the genus Artemia.

7. The isolated nucleic acid according to any one of claims 1 through 4 wherein said isolated nucleic acid is DNA.

8. The isolated nucleic acid according to claim 1 wherein said amino acid sequence is an Artemia MT protein.

9. A vector comprising a nucleic acid comprising the nucleotide sequence of SEQ. ID. NO. 1 or SEQ. ID. NO. 3.

10. The vector according the claim 9 further comprising at least one control sequence that controls the expression or regulation of said nucleic acid.

11. The vector according to claim 10 wherein said control sequence is selected from the group consisting of an operator, a promoter, an enhancer, and a promoter-proximal elements.

12. A modified host cell comprising the vector according to claim 9 or 10.

13. The modified host cell according to claim 12 wherein said host cell is selected from the group consisting of a bacterium, a yeast, an alga, and a mammalian cell.

14. The modified host cell according to claim 13 wherein said nucleic acid expresses an Artemia MT protein or metal binding amino acid sequence.

15. An isolated nucleic acid consisting essentially of the nucleotide sequence of SEQ. ID. NO. 1.

16. An isolated nucleic acid consisting essentially of the nucleotide sequence of SEQ. ID. NO. 3.

* * * * *

UNITED STATES PATENT AND TRADEMARK OFFICE
CERTIFICATE OF CORRECTION

PATENT NO. : 6,750,056 B2
DATED : June 15, 2004
INVENTOR(S) : Roger A. Acey, Michael Mustillo and Brenda G. Harpham It is certified that error appears in the above-identified patent and that said Letters Patent is hereby corrected as shown below:

Column 16,
Line 51, replace "KCL" with -- KCI --.

Column 20,
Line 13, replace "Mt" with -- MT --.
Line 17, replace "subdloned" with -- subcloned --.

Signed and Sealed this

Nineteenth Day of April, 2005

JON W. DUDAS
*Director of the United States Patent and Trademark Office*